(12) United States Patent  
Miyaki

(10) Patent No.: US 8,123,690 B2  
(45) Date of Patent: Feb. 28, 2012

(54) ULTRASOUND OBSERVATION APPARATUS

(75) Inventor: Hironaka Miyaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 321 days.

(21) Appl. No.: 12/437,930

(22) Filed: May 8, 2009

(65) Prior Publication Data

US 2009/0281426 A1    Nov. 12, 2009

(30) Foreign Application Priority Data

May 8, 2008    (JP) ................................. 2008-122264

(51) Int. Cl.
*A61B 8/00*    (2006.01)
(52) U.S. Cl. ......... 600/437; 600/426; 600/454; 600/441
(58) Field of Classification Search .................. 600/437, 600/426, 454, 441

See application file for complete search history.

(56) References Cited

U.S. PATENT DOCUMENTS 5,081,996 A    1/1992    Kawasaki et al.

(Continued)

FOREIGN PATENT DOCUMENTS

EP    1 138 262 A2    10/2001

(Continued)

OTHER PUBLICATIONS

Japanese Office Action dated Dec. 8, 2009.

*Primary Examiner* — Brian Casler
*Assistant Examiner* — Joel Lamprecht
(74) *Attorney, Agent, or Firm* — Scully, Scott, Murphy & Presser, P.C.

(57) ABSTRACT

An ultrasound observation apparatus of the present invention is an ultrasound observation apparatus capable of creating a blood flow image of a subject by receiving a reflection signal of a sound output signal transmitted to the subject as an electric signal, and performing various kinds of signal processing for the electric signal, and includes a transmission frequency switching section switching a frequency band of the sound output signal which is transmitted to the subject to a frequency band corresponding to an instruction signal which is outputted from an operation instructing section, and a blood flow color creating section changing a color at a time of visualizing the blood flow image by linking with switching of the frequency band by the transmission frequency switching section.

9 Claims, 6 Drawing Sheets

U.S. PATENT DOCUMENTS

| | | |
|---|---|---|
| 5,891,040 A | 4/1999 | Grenon et al. |
| 6,248,073 B1 | 6/2001 | Gilbert et al. |
| 6,287,258 B1 | 9/2001 | Phillips |
| 6,679,843 B2 * | 1/2004 | Ma et al. ............... 600/441 |
| 6,685,636 B2 * | 2/2004 | Okabayashi et al. ......... 600/437 |

FOREIGN PATENT DOCUMENTS

| | | |
|---|---|---|
| JP | 63-315038 | 12/1988 |
| JP | 2000-316861 | 11/2000 |
| JP | 2001-340338 | 12/2001 |

* cited by examiner

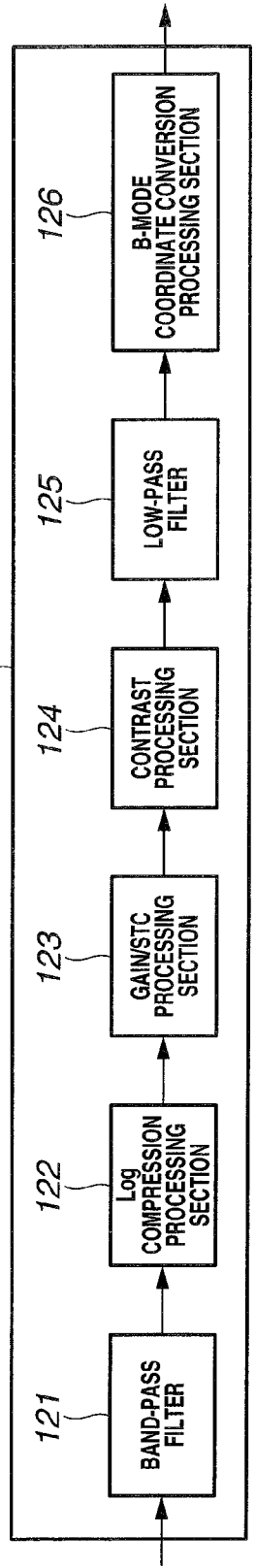
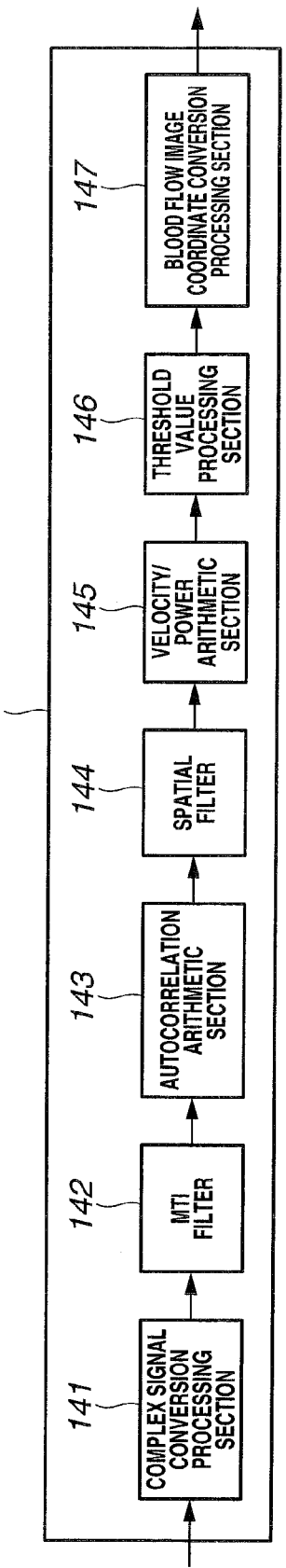

FIG.4

| 1/6 | 1/6 |
|-----|-----|
| 1/6 | 1/6 |
| 1/6 | 1/6 |

FIG.5

| 1/4 | 1/4 |
|-----|-----|
| 1/4 | 1/4 |

FIG.6

| 0 | 0 | 1/13 | 0 | 0 |
|---|---|---|---|---|
| 0 | 1/13 | 1/13 | 1/13 | 0 |
| 1/13 | 1/13 | 1/13 | 1/13 | 1/13 |
| 0 | 1/13 | 1/13 | 1/13 | 0 |
| 0 | 0 | 1/13 | 0 | 0 |

FIG.7

| 0 | 1/5 | 0 |
|---|---|---|
| 1/5 | 1/5 | 1/5 |
| 0 | 1/5 | 0 |

ULTRASOUND OBSERVATION APPARATUS

This application claims benefit of Japanese Application No. 2008-122264 filed in Japan on May 8, 2008, the contents of which are incorporated by this reference.

BACKGROUND OF THE INVENTION

1. Field of the Invention

The present invention relates to an ultrasound observation apparatus, and particularly relates to an ultrasound observation apparatus capable of creating a blood flow image of a subject.

2. Description of the Related Art

An ultrasound observation apparatus has been conventionally used widely, which can obtain a tomographic image of a living body, and a blood flow image of an inside of a region of interest of the tomographic image by transmitting ultrasound into the living body as a subject and receiving reflection wave which is the ultrasound reflected in a biological tissue as an examined region in the living body. Further, the tomographic image and the blood flow image of the living body which are obtained by the aforementioned ultrasound observation apparatus are used, for example, when an operator and the like observe penetration depths of lesions, or observe a state of an inside of an organ. As the apparatus having such a function, there is proposed an ultrasound diagnostic apparatus of, for example, U.S. Pat. No. 6,419,632.

U.S. Pat. No. 6,419,632 discloses a configuration for making it possible to acquire a blood flow image of a microvessel existing in the subject by transmitting an ultrasound pulse having a wide-band frequency characteristic and performing predetermined signal processing for an echo signal which is the ultrasound pulse reflected in the subject, in the ultrasound diagnostic apparatus.

SUMMARY OF THE INVENTION

An ultrasound observation apparatus in the present invention is an ultrasound observation apparatus capable of creating a blood flow image of a subject by receiving a reflection signal of a sound output signal transmitted to the subject as an electric signal, and performing various kinds of signal processing for the electric signal, and includes a transmission frequency switching section switching a frequency band of the sound output signal which is transmitted to the subject to a frequency band corresponding to an instruction signal which is outputted from an operation instructing section, and a blood flow color creating section changing a color at a time of visualizing the blood flow image by linking with switching of the frequency band by the transmission frequency switching section.

An ultrasound observation apparatus in the present invention is an ultrasound observation apparatus capable of creating a blood flow image of a subject by receiving a reflection signal of a sound output signal transmitted to the subject as an electric signal, and performing various kinds of signal processing for the electric signal, and includes a transmission frequency switching section switching a frequency band of the sound output signal which is transmitted to the subject to a frequency band corresponding to an instruction signal which is outputted from an operation instructing section, and a filter processing section performing spatial filter processing at a time of creation of the blood flow image, and changing a processing content of the spatial filter processing by linking with switching of the frequency band by the transmission frequency switching section.

BRIEF DESCRIPTION OF THE DRAWINGS

FIG. 2 is a block diagram showing one example of a detailed configuration of a B-mode image arithmetic section included by the ultrasound observation apparatus of FIG. 1;

FIG. 3 is a block diagram showing one example of a detailed configuration of a blood flow image arithmetic section included by the ultrasound observation apparatus of FIG. 1;

FIG. 4 is a diagram showing one example of a filter coefficient which is set in a spatial filter included by the blood flow image arithmetic section of FIG. 3;

FIG. 5 is a diagram showing an example, which is different from FIG. 4, of the filter coefficient which is set in the spatial filter included by the blood flow image arithmetic section of FIG. 3;

FIG. 6 is a diagram showing one example of the filter coefficient which is set in a spatial filter provided at a post-stage of the blood flow image arithmetic section of FIG. 1;

FIG. 7 is a diagram showing an example, which is different from FIG. 6, of the filter coefficient which is set in the spatial filter provided at the post-stage of the blood flow image arithmetic section of FIG. 1;

DETAILED DESCRIPTION OF THE PREFERRED EMBODIMENTS

Hereinafter, an embodiment of the present invention will be described with reference to the drawings.

Figure 1:
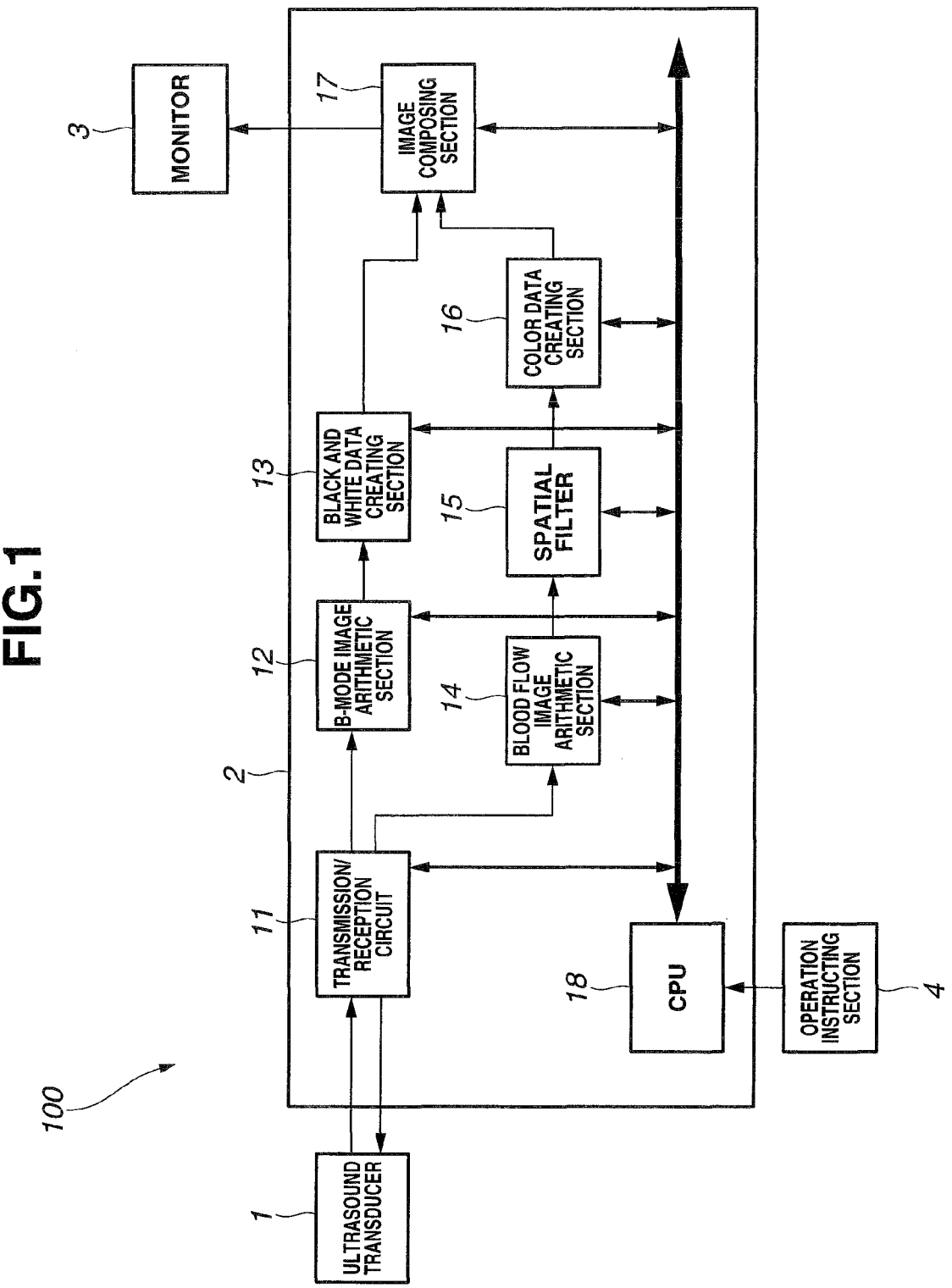
FIG. 1 is a diagram showing one example of a configuration of an essential part of an ultrasound observation system including an ultrasound observation apparatus according to an embodiment of the present invention.

FIGS. 1 to 11 relate to the embodiment of the present invention. FIG. 1 is a diagram showing one example of a configuration of an essential part of an ultrasound observation system including an ultrasound observation apparatus according to the embodiment of the present invention. FIG. 2 is a block diagram showing one example of a detailed configuration of a B-mode image arithmetic section included by the ultrasound observation apparatus of FIG. 1. FIG. 3 is a block diagram showing one example of a detailed configuration of a blood flow image arithmetic section included by the ultrasound observation apparatus of FIG. 1. FIG. 4 is a diagram showing one example of a filter coefficient which is set in a spatial filter included by the blood flow image arithmetic section of FIG. 3. FIG. 5 is a diagram showing an example, which is different from FIG. 4, of the filter coefficient which is set in the spatial filter included by the blood flow image arithmetic section of FIG. 3. FIG. 6 is a diagram showing one example of the filter coefficient which is set in a spatial filter provided at a post-stage of the blood image arithmetic section of FIG. 1. FIG. 7 is a diagram showing an example, which is different from FIG. 6, of the filter coefficient which is set in the spatial filter provided at the post-stage of the blood image arithmetic section of FIG. 1.

Figures 8A, 8B:
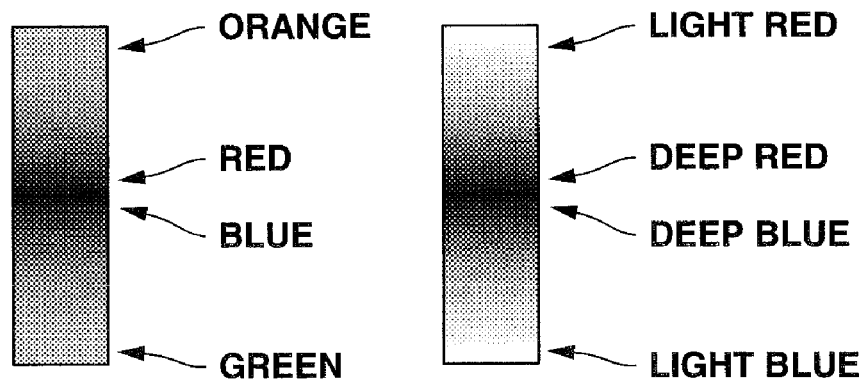
FIG. 8A is a diagram showing one example of a color palette included by a color data creating section of FIG. 1.
FIG. 8B is a diagram showing an example, which is different from FIG. 8A, of the color palette included by the color data creating section of FIG. 1.
Figures 9A, 9B:
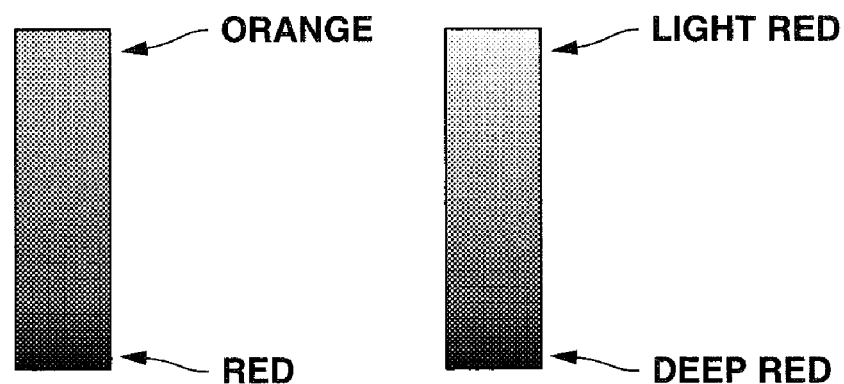
FIG. 9A is a diagram of an example, which is different from FIGS. 8A and 8B, of the color palette included by the color data creating section of FIG. 1.
FIG. 9B is a diagram showing an example, which is different from FIGS. 8A, 8B and 9A, of the color palette included by the color data creating section of FIG. 1.
Figure 10:
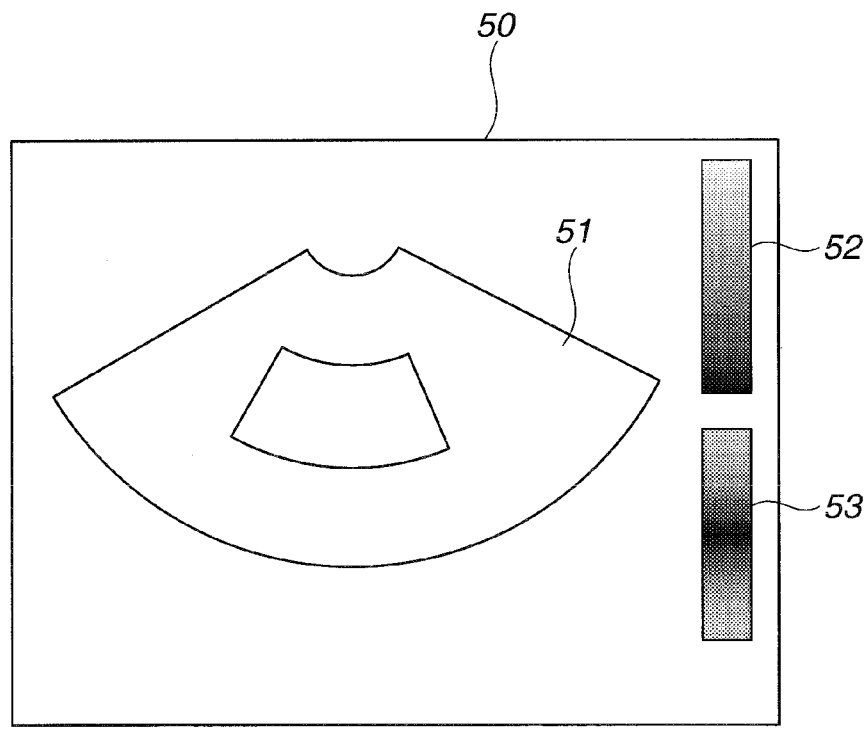
FIG. 10 is a diagram showing one example of an image which is outputted to a monitor from the ultrasound observation apparatus of FIG. 1.
Figure 11:
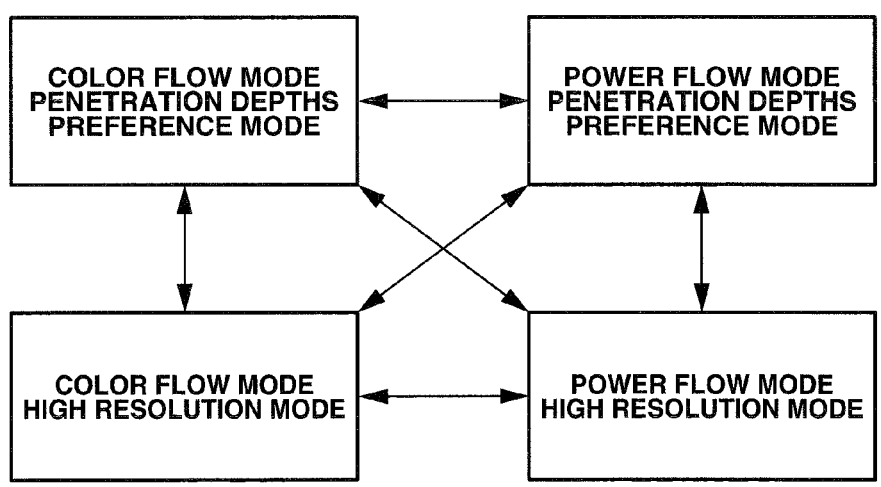
FIG. 11 is a diagram for explaining transition among display modes of a blood flow image.

FIG. 8A is a diagram showing one example of a color palette included by a color data creating section of FIG. 1. FIG. 8B is a diagram showing an example, which is different from FIG. 8A, of the color palette included by the color data creating section of FIG. 1. FIG. 9A is a diagram of an example, which is different from FIGS. 8A and 8B, of the color palette included by the color data creating section of FIG. 1. FIG. 9B is a diagram showing an example, which is different from FIGS. 8A, 8B and 9A, of the color palette included by the color data creating section of FIG. 1. FIG. 10 is a diagram showing one example of an image which is outputted to a monitor from the ultrasound observation apparatus of FIG. 1. FIG. 11 is a diagram for explaining transition among display modes of a blood flow image.

An ultrasound observation system 100 has an essential part configured by having an ultrasound transducer 1, an ultrasound observation apparatus 2 which performs processing for an electric pulse signal from the ultrasound transducer 1 and outputs the electric pulse signal after processing as an video signal, a monitor 3 which performs image display based on the video signal which is outputted from the ultrasound observation apparatus 2, and an operation instructing section 4 capable of outputting an instruction signal for giving instructions to each section of the ultrasound observation system 100, as shown in FIG. 1.

The ultrasound transducer 1 configured by a plurality of array transducers converts an electric pulse signal which is outputted from the ultrasound observation apparatus 2 into a sound pulse signal, and transmits the sound pulse signal to a subject (not illustrated). Further, the ultrasound transducer 1 receives a sound reflection signal which generates as a result of the sound pulse signal transmitted to the subject being reflected in the subject, and converts scanning information of each sound ray based on the sound reflection signal into an electric pulse signal to output the electric pulse signal to the ultrasound observation apparatus 2.

The ultrasound transducer 1 of the present embodiment may be configured by the other elements than a plurality of array transducers. (In this case, a transmission/reception circuit 11 which will be described later has the configuration which does not include a beam forming circuit.)

The ultrasound observation apparatus 2 has a transmission/reception circuit 11 including a function as a transmission frequency switching section, a B-mode image arithmetic section 12, a black and white data creating section 13, a blood flow image arithmetic section 14, a spatial filter 15 which configures a part of a filter processing section, a color data creating section 16 including a function as a blood flow color creating section, an image composing section 17 connected to the monitor 3, and a CPU 18 connected to the operation instructing section 4, as shown in FIG. 1.

The transmission/reception circuit 11 is configured by including a pre-amplifier, an A/D conversion circuit, and a beam forming circuit. The transmission/reception circuit 11 creates an electric pulse with a center frequency and the number of pulse waves corresponding to control of the CPU 18, and outputs the electric pulse to the ultrasound transducer 1. Further, the transmission/reception circuit 11 creates digital RF data by performing amplification and A/D conversion processing for the electric pulse signal from the ultrasound transducer 1, and thereby, creates digital RF data. The transmission/reception circuit 11 outputs the created digital RF data for B-mode image creation to the B-mode image arithmetic section 12, and outputs the one for blood image creation to the blood flow image arithmetic section 14 out of the generated digital RF data.

The B-mode image arithmetic section 12 has a band-pass filter 121, a Log compression processing section 122, a gain/STC processing section 123, a contrast processing section 124, a low-pass filter 125, and a B-mode coordinate conversion processing section 126 which are respectively constructed by using known techniques. The digital RF data outputted to the B-mode image arithmetic section 12 is outputted to the black and white data creating section 13 by being brought into a state converted into the B-mode image data by being sequentially subjected to the processing by each of the aforementioned sections. The B-mode image data which is calculated by the B-mode image arithmetic section 12 may be two-dimensional data or three-dimensional data.

The black and white data creating section 13 is configured as a lookup table (hereinafter, called an LUT) for showing correspondence of the value of the B-mode image data and three-color data configured by Red, Green and Blue which are stored in a RAM or a ROM. The B-mode image data from the B-mode image arithmetic section 12 passes through the black and white data creating section 13 of the aforementioned configuration, and thereby, is outputted to the image composing section 17 as the state converted into black and white data of a predetermined gradation.

The blood flow image arithmetic section 14 has a function of being able to create image data based on a velocity value, or a power value of blood flow. (The blood flow in the description of the present embodiment is used as the word having a wide meaning including flow of an artificial reflector injected into a blood vessel as, for example, an ultrasound contrast medium.) More specifically, as shown in FIG. 3, the blood flow image arithmetic section 14 has a complex signal conversion processing section 141, an MTI filter 142, an auto-correlation arithmetic section 143, a spatial filter 144 configuring a part of the filter processing section, a velocity/power arithmetic section 145, a threshold value processing section 146 and a blood flow image coordinate conversion processing section 147.

More specifically, the filter processing section in the present embodiment is configured by including the spatial filter 144 and the spatial filter 15.

The complex signal conversion processing section 141 has a configuration capable of converting the digital RF data which is outputted from the transmission/reception circuit 11 into a complex signal, and outputting the complex signal. More specifically, the complex signal conversion processing section 141 is configured by including a so-called quadrature detector which can obtain a complex signal by performing processing of multiplying sine wave signals differing in phase by 90 degrees from each other and passing the result through the low-pass filter for digital RF data in sequence.

The complex signal conversion processing section 141 is not limited to the one configured by including a quadrature detector, but may be configured by including a so-called quadrature sampling device which can obtain a complex signal by performing processing of sampling by using data at a certain time which are in the relation differing from each other in phase by 90 degrees in a center frequency of the digital RF data, for example, as a real number signal and an imaginary number signal. Further, the complex signal conversion processing section 141 is not limited to the one configured by including a quadrature detector, but may include a configuration which can obtain a complex signal from digital RF data by performing signal processing using, for example, a Hilbert transform filter. Further, processing for obtaining a complex signal in the complex signal conversion processing section 141 may be realized by using hardware such as FPGA, or may be realized by using software (program) written in a DSP or CPU.

Incidentally, when the ultrasound observation apparatus 2 operates in the mode of displaying the velocity value or the power value of blood flow, a sound pulse signal with a predetermined frequency is transmitted predetermined times (for example, eight times) along one sound ray direction which is a detection target of the blood flow, and thereafter, sound reflection signals of the predetermined times reflected in the one sound ray direction are received. At this time, in the aforementioned one sound ray direction, complex signal groups as many as the aforementioned predetermined times (for example, eight) are obtained in the point at the same depth. By performing the same processing while sequentially changing the sound ray direction to be the detection target of blood flow, complex signal groups as many as the aforementioned predetermined times can be obtained at each point on a two-dimensional local plane, or in a three-dimensional local space. The complex signal groups thus obtained are temporarily stored in a memory not illustrated provided in the ultrasound observation apparatus 2.

The MTI filter 142 includes a digital FIR filter or an IIR filter which is constructed by using any of a DSP, CPU and FPGA. When the MTI filter 142 is constructed by a DSP, floating point arithmetic processing may be performed.

The MTI filter 142 reads one or a plurality of complex signal groups which is or are acquired in a predetermined space position on one sound ray from the aforementioned memory not illustrated, and thereafter, performs filter processing for removing low-frequency components (components with less variation) for a real number signal group and an imaginary number signal group configuring the one or plurality of complex signal groups. (Such filter processing corresponds to processing for removing a component at a low velocity from a sound reflection signal.)

The MTI filter 142 outputs as many complex signal groups as the number of the signals at the time of input from which the portions corresponding to transition response of the filter are removed, which are created by combining the real number signal groups and the imaginary number signal groups after being subjected to the aforementioned filter processing to the autocorrelation arithmetic section 143.

The autocorrelation arithmetic section 143 calculates the complex autocorrelation value of the complex signal group based on the complex signal group which is outputted from the MTI filter 142. The autocorrelation arithmetic section 143 may calculate the aforementioned complex autocorrelation value by hardware such as FPGA, or may calculate the aforementioned complex autocorrelation value by using software (program) written in a DSP or a CPU.

Here, a complex signal group $Z_i$ which is outputted from the MTI filter 142 is defined as the following equation (1) (where i=1 to N).

$$z_i = x_i + j y_i \quad (1)$$

In this case, the complex autocorrelation value R is expressed as in the following equation (2).

$$R = \sum_{i=1}^{N-1} z_i \times z_{i+1} * \quad (2)$$

In the above described equation (2), * expresses complex conjugate.

More specifically, the autocorrelation arithmetic section 143 calculates and outputs a complex autocorrelation value R shown as the above described equation (2) based on the complex signal group which is outputted from the MTI filter 142.

The spatial filter 144 performs spatial filter processing for the complex autocorrelation value R while using a filter type, the number of filter taps and a filter coefficient designated by the CPU 18. Further, the spatial filter 144 can perform processing of directly outputting the inputted complex autocorrelation value R without performing the aforementioned spatial filter processing in accordance with the instruction from the CPU 18.

The spatial filter 144 may be the one that performs the aforementioned spatial filter processing by the hardware such as FPGA, or may be the one that performs the aforementioned spatial filter processing by using software (program) written in the DSP or CPU.

For the aforementioned spatial filter processing by the spatial filter 144, spatial filters as in FIGS. 4 and 5 are used, for example. More specifically, FIG. 4 shows one example of the filter coefficient in the case of the linear smoothing filter and the number of filter taps of 2×3. FIG. 5 shows one example of the filter coefficient in the case of the linear smoothing filter and the number of filter taps of 2×2. At the time of the aforementioned spatial filter processing by the spatial filter 144, the filters including the filter types, the numbers of filter taps and the filter coefficients other than those shown as examples in FIGS. 4 and 5 may be selected.

The spatial filter processing as described above is performed in the spatial filter 144, whereby an electric noise component which appears as a spatially random value in the complex autocorrelation value R can be suppressed.

The velocity/power arithmetic section 145 is configured by an FPGA, DSP, CPU or the like, and calculates the velocity value or the power value of the blood flow based on the complex autocorrelation value R outputted from the spatial filter 144. More specifically, the velocity/power arithmetic section 145 calculates the velocity value v of the blood flow based on the complex autocorrelation value R outputted from the spatial filter 144 and the following equation (3).

$$v = \frac{c}{4\pi f_0 T} \tan^{-1}\left(\frac{Ry}{Rx}\right) \quad (3)$$

In the above described equation (3), c represents a sound velocity, $f_0$ represents a center frequency of the electric pulse transmitted and received, T represents a time cycle when transmission and reception are repeated in the same sound ray direction, Rx represents a real number component of the complex autocorrelation value R, and Ry represents an imaginary number component of the complex autocorrelation value R.

Meanwhile, the velocity/power arithmetic section 145 calculates a power value I of the blood flow as an absolute value of the complex autocorrelation value R based on the complex autocorrelation value R which is outputted from the spatial filter 144, and the following equation (4).

$$I=|R| \quad (4)$$

The threshold value processing section 146 is configured by an FPGA, DSP, CPU or the like, and judges whether or not color display of the velocity value or the power value of the blood flow in one spatial position is performed on the monitor 3. More specifically, the threshold value processing section 146 detects whether or not the velocity value v and the power value I in one spatial position, for example, satisfy all the conditions of the following expressions (5), (6) and (7).

$$|v|>V_{TH} \quad (5)$$

$$I>I_{TH1} \quad (6)$$

$$I<I_{TH2} \quad (7)$$

$V_{TH}$ in the above described expression (5) represents a threshold value relating to the velocity value. $I_{TH1}$ in the above described expression (6) represents a threshold value corresponding to the power of noise included in the received electric pulse. $I_{TH2}$ in the above described expression (7) represents a threshold value corresponding to the power of the living tissue included in the received electric pulse. Further, the optimal value in each of the threshold values can be properly set in accordance with the transmission and reception sensitivity of the ultrasound transducer 1, the noise level of the internal circuit of the ultrasound observation apparatus 2 and the like.

When the velocity value v and the power value I in one spatial position satisfy all the conditions of the above described expressions (5), (6) and (7), the threshold value processing section 146 performs color display of the velocity value v or the power value I in the one spatial position. Further, when the velocity value v and the power value I in one spatial position do not satisfy at least any one condition of the above described expressions (5), (6) and (7), the threshold value processing section 146 performs processing of substituting zero for the values so that color display of the velocity value v or the power value I in the one spatial position is not performed.

The blood flow image coordinate conversion processing section 147 creates a two-dimensional or three-dimensional image by applying coordinate conversion processing to the velocity value v or the power value I which is outputted from the threshold value processing section 146.

The velocity value v or the power value I which is outputted from the threshold value processing section 146 is generally image data in the form of polar coordinates. Specifically, the blood flow image coordinate conversion processing section 147 converts the image data in the polar coordinates form which is outputted from the threshold value processing section 146 into the image data in the orthogonal coordinate form suitable for display in the monitor 3, by performing the aforementioned coordinate conversion processing.

The spatial filter 15 performs spatial filter processing for the image data of the blood flow image which is outputted from the blood flow image coordinate conversion processing section 147 while using the filter type, the number of filter taps and the filter coefficient designated by the CPU 18.

The data dealt in the spatial filter 15 is a scalar quantity unlike the data dealt in the spatial filter 144. Further, the spatial filter 15 is disposed at the post-stage of the blood flow image coordinate conversion processing section 147 unlike the spatial filter 144 disposed at the pre-stage of the blood flow image coordinate conversion processing section 147.

For the aforementioned spatial filter processing by the spatial filter 15, spatial filters as in FIGS. 6 and 7, for example, are used. More specifically, FIG. 6 shows one example of the filter coefficient in the case of the linear smoothing filter and the number of filter taps of 5×5. Further, FIG. 7 shows one example of the filter coefficient in the case of the linear smoothing filter and the number of filter taps of 3×3. At the time of the aforementioned spatial filter processing by the spatial filter 15, a smoothing filter of another type such as a median filter may be used, or the filter including the number of filter taps and the filter coefficient other than those shown as examples in FIGS. 6 and 7 may be selected.

The spatial filter processing as described above is performed in the spatial filter 15, whereby the edge of the blood flow image after being converted into the orthogonal coordinate form is rounded, and the pixels in the blood flow image can be smoothly connected.

The color data creating section 16 is configured as the one in which a plurality LUTs, which correspond to a plurality of color palettes configured by the combination of the colors which can be expressed by using at least one color of Red, Green and Blue, are stored in the RAM or ROM. The color data creating section 16 selects one color palette from the aforementioned plurality of color palettes based on the instruction of the CPU 18, and thereafter, converts the image data of the blood flow image which is outputted from the spatial filter 15 into color data for display while referring to the one color palette and outputs the color data.

As a concrete example, the color data creating section 16 uses the color palette shown in FIG. 8A when mainly assigning the velocity value of blood flow to change in hue, and uses the color palette shown in FIG. 8B when mainly assigning the velocity value of blood flow to change in color saturation (color) to create color data, based on instruction of the CPU 18. Further, the color data creating section 16 uses the color palette shown in FIG. 9A when mainly assigning the power value of blood flow to change in hue, and uses the color palette shown in FIG. 9B when mainly assigning the power value of blood flow to change in color saturation (color) to create color data, based on instruction of the CPU 18.

The image composing section 17 creates image data for display by composing the black and white data which is outputted from the black and white data creating section 13, and the color data outputted from the color data creating section 16.

More specifically, the image composing section 17 creates image data for display by overwriting color data onto black and white data in each of the positions including the other data values than the data values with one of the velocity value and the power value corresponding to zero, among the color data outputted from the color data creating section 16.

The image composing section 17 may prohibit overwriting of color data onto the black and white data when a predetermined condition is satisfied based on the comparison result of comparing the size relation of the color data and the black and white data, or the comparison result of comparing the color data and the black and white data with the individual threshold values. Further, when the display mode of the ultrasound observation apparatus 2 is not set to any mode of the velocity value and the power value of blood flow, the image composing section 17 creates black and white data as the image data for display without composing the black and white data and the color data.

The monitor 3 displays the image corresponding to the image data for display which is outputted from the image composing section 17, for example, the image shown in FIG. 10, on the screen.

The image 50 for display displayed on the monitor 3 is configured by including at least an ultrasound image display section 51, a gray scale display section 52 and a color scale display section 53 as shown in FIG. 10.

The ultrasound image display section 51 collectively displays the image data for display outputted from the image composing section 17, character information not illustrated and the like.

The gray scale display section 52 displays the gray scale which is used when the B-mode image data is converted into black and white data for monitor display by the black and white data creating section 13.

The color scale display section 53 displays a color palette, which is used when the velocity value or the power value of blood flow is converted into the color data for monitor display by the color data creating section 16.

The operation instructing section 4 includes a keyboard, a push-button switch, a track ball, a touch panel and the like which can output instruction signals for giving instructions to each of the sections of the ultrasound observation system 100 to the CPU 18.

Next, an operation of the ultrasound observation system 100 including the ultrasound observation apparatus 2 of the present embodiment will be described.

First, an operator selects one of the color flow mode and the power flow mode as the display mode of the blood flow information, and selects resolution of the blood flow image, by operation of the operation instructing section 4.

Hereinafter, an example capable of switching two modes that are a penetration depths preference mode and a high resolution mode as the resolution of the blood flow image will be mainly described. In other words, in the present embodiment, an example which is capable of selecting the combination of the display mode and resolution of blood flow information from four combinations shown in FIG. 11 and capable of switching the combination to one of the four combinations will be mainly described.

In the present embodiment, as the resolution of the blood flow image, in addition to the two modes that are the penetration depths preference mode and the high resolution mode, a normal mode which is an intermediate mode between the two modes, for example, may be further provided.

The CPU 18 performs control relating to setting of the center frequency and the number of pulse waves of the electric pulse which is outputted to the ultrasound transducer 1 for blood flow image acquisition for the transmission/reception circuit 11 on the basis of the instruction signals which are outputted from the operation instructing section 4 in correspondence with selection of the display mode of the blood flow information and resolution of the blood flow image.

More specifically, the CPU 18 makes setting so as to transmit the electric pulse with the center frequency of 5 MHz and the number of pulse waves of three when, for example, the combination of the color flow mode and the penetration depths preference mode is selected, and makes setting so as to transmit the electric pulse with the center frequency of 7.5 MHz and the number of pulse waves of two when the combination of the color flow mode and the high resolution mode is selected.

The center frequency and the number of pulse waves are switched as described above, whereby in the case of the high resolution mode, the frequency band of the sound pulse signal which is transmitted to the subject from the ultrasound transducer 1 becomes wide, and shifts to the high frequency side, and therefore, resolution to the propagating direction of the sound pulse is improved. More specifically, when the ultrasound observation apparatus 2 is switched to the high resolution mode, detectability of a micro-vessel existing in the subject is improved. Further, setting of the center frequency and the number of pulse waves is made different between the color flow mode and the power flow mode, detectability of a micro-vessel between both the modes can be changed.

In the ultrasound observation apparatus 2 of the present embodiment, the resolution of the B-mode image can be switched separately from the resolution of the blood flow image. More specifically, the CPU 18 makes setting for the transmission/reception circuit 11 so that the electric pulse, for example, with the center frequency of 7.5 MHz and the number of pulses of one wave is outputted to the ultrasound transducer 1 as the setting for B-mode image acquisition, based on the instruction signal which is outputted from the operation instructing section 4 in correspondence with selection of the resolution of the B-mode image.

Next, the CPU 18 performs setting of the value of $f_0$ which is used at the time of calculation of the above described equation (3) to the velocity/power arithmetic section 145 in the blood flow image arithmetic section 14.

More specifically, the CPU 18 sets $f_0$=5 MHz when the penetration depths preference mode is selected, and sets $f_0$=7.5 MHz when the high resolution mode is selected.

Thereafter, the CPU 18 gives instructions relating to setting of the filter type, the number of filter taps and filter coefficient corresponding to the resolution of the blood flow image to the spatial filter 144.

More specifically, the CPU 18 gives an instruction for using the linear smoothing filter of 2×3 including the coefficient shown in FIG. 4 when the combination of the color flow mode and the penetration depths preference mode is selected, and gives an instruction for directly outputting inputted data without performing spatial filter processing when the combination of the color flow mode and the high resolution mode is selected.

Further, the CPU 18 gives an instruction for using the linear smoothing filter of 2×2 including the coefficient shown in FIG. 5 when the combination of the power flow mode and the penetration depths preference mode is selected, and gives an instruction for directly outputting the inputted data without performing spatial filter processing when the combination of the power flow mode and the high resolution mode is selected.

Switching of the filter as described above is performed in the spatial filter 144, whereby noise included in the received electric pulse can be reduced in the case of the penetration depths preference mode. Further, switching of the spatial filter as described above is performed in the spatial filter 144, whereby in the case of the high resolution mode, deterioration of the spatial resolution does not occur, and as a result, detectability of a micro-vessel existing in the subject can be improved.

Meanwhile, the CPU 18 gives an instruction relating to setting of the filter type, the number of filter taps and filter coefficient corresponding to the resolution of the blood flow image to the spatial filter 15.

More specifically, the CPU 18 gives an instruction for using the linear smoothing filter of 5×5 including the coefficient shown in FIG. 6 when the combination of the color flow mode and the penetration depths preference mode is selected, and gives an instruction for using the median filter of 3×3 when the combination of the color flow mode and the high resolution mode is selected.

Further, the CPU 18 gives an instruction for using the linear smoothing filter of 3×3 including the coefficient shown in FIG. 7 when the combination of the power flow mode and the penetration depths preference mode is selected, and gives an instruction for using a median filter of 3×3 when the combination of the power flow mode and the high resolution mode is selected.

Subsequently, switching of the filter as described above is performed in the spatial filter 15, whereby, in the case of the high resolution mode, the edge of the blood flow image which is displayed on the screen of the monitor 3 hardly blurs, and visualization of a micro-vessel is improved. Therefore, the divergence state of a micro-vessel can be faithfully expressed.

The CPU 18 gives an instruction relating to switching of the color palette corresponding to the resolution of a blood flow image to the color data creating section 16.

More specifically, the CPU 18 gives an instruction for using the color palette of FIG. 8A when the combination of the color flow mode and the penetration depths preference mode is selected, and gives an instruction for using the color palette of FIG. 8B when the combination of the color flow mode and the high resolution mode is selected.

Further, the CPU 18 gives an instruction for using the color palette of FIG. 9A when the combination of the power flow mode and the penetration depths preference mode is selected, and gives an instruction for using the color palette of FIG. 9B when the combination of the power flow mode and the high resolution mode is selected. In the present embodiment, the display state of the color scale display section 53 is changed by being linked with the instruction for switching the color palette by the CPU 18.

Switching of the color palette as described above is performed in the color data creating section 16, whereby visualization of a micro-vessel in the case of the high resolution mode can be improved. Further, in the present embodiment, the display state of the color scale display section 53 is switched by being linked with selection of the resolution, and therefore, an operator can easily recognize setting of the resolution which is selected at present.

As described above, according to the ultrasound observation apparatus 2 according to the present embodiment, the elements of the frequency band of the transmission pulse, the processing content in each of the two spatial filters, and the coloring state of the color data are switched respectively by being linked to the switching operation of the resolution of the blood flow image. As a result, according to the ultrasound observation apparatus 2 according to the present embodiment, detectability and visualization of micro-vessels can be improved by the simple operation as compared with the conventional apparatuses.

The present invention is not limited to the above described each embodiment, and it goes without saying that various modifications and applications can be made within the range without departing from the spirit of the invention.

What is claimed is:

1. An ultrasound observation apparatus capable of creating a blood flow image of a subject by receiving a reflection signal of a sound output signal transmitted to the subject as an electric signal, and performing various kinds of signal processing for the electric signal, comprising:

a transmission frequency switching section that switches a frequency band of the sound output signal which is transmitted to the subject to a frequency band corresponding to a combination of a display mode and resolution of the blood flow image, the display mode including a color flow mode for displaying the blood flow image based on a velocity value of blood flow and a power flow mode for displaying the blood flow image based on a power value of the blood flow; and a blood flow color creating section that selects one color palette from a plurality of color palettes by linking with switching of the frequency band by the transmission frequency switching section and changes a color at a time of visualizing the blood flow image using the one color palette.

2. The ultrasound observation apparatus according to claim 1, wherein the blood flow color creating section changes one of hue and color saturation at a time of visualizing the blood flow image using the one color palette selected by linking with switching of the frequency band by the transmission frequency switching section.

3. An ultrasound observation apparatus capable of creating a blood flow image of a subject by receiving a reflection signal of a sound output signal transmitted to the subject as an electric signal, and performing various kinds of signal processing for the electric signal, comprising:

a transmission frequency switching section that switches a frequency band of the sound output signal which is transmitted to the subject to a frequency band corresponding to a combination of a display mode and resolution of the blood flow image, the display mode including a color flow mode for displaying the blood flow image based on a velocity value of blood flow and a power flow mode for displaying the blood flow image based on a power value of the blood flow; and a filter processing section including a first spatial filter and a second spatial filter, the first spatial filter being provided at a pre-stage side of a coordinate conversion processing section which converts a coordinate form of the blood flow image into orthogonal coordinates from polar coordinates and configured to perform first filter processing for suppressing a noise component included in the electric signal, and the second spatial filter being provided at a post-stage side of the coordinate conversion processing section and configured to perform second filter processing for smoothing an edge of the blood flow image, the filter processing section being configured to change processing contents of at least one of the first filter processing and the second filter processing by linking with switching of the frequency band by the transmission frequency switching section.

4. The ultrasound observation apparatus according to claim 3, wherein at least one of a filter type, the number of filter taps and a filter coefficient used for filter processing in either the first filter processing or the second filter processing is changed by linking with switching of the frequency band by the transmission frequency switching section.

5. The ultrasound observation apparatus according to claim 3, wherein at least one of a filter type, the number of filter taps and a filter coefficient used for filter processing in both the first filter processing and the second filter processing is changed by linking with switching of the frequency band by the transmission frequency switching section.

6. An ultrasound observation apparatus capable of creating a blood flow image of a subject by receiving a reflection signal of a sound output signal transmitted to the subject as an electric signal, and performing various kinds of signal processing for the electric signal, comprising:

a transmission frequency switching section that switches a frequency band of the sound output signal which is transmitted to the subject to a frequency band corresponding to a combination of a display mode and resolution of the blood flow image, the display mode including a color flow mode for displaying the blood flow image based on a velocity value of blood flow and a power flow mode for displaying the blood flow image based on a power value of the blood flow;

a blood flow color creating section that selects one color palette from a plurality of color palettes by linking with switching of the frequency band by the transmission frequency switching section and changes a color at a time of visualizing the blood flow image using the one color palette; and a filter processing section including a first spatial filter and a second spatial filter, the first spatial filter being provided at a pre-stage side of a coordinate conversion processing section which converts a coordinate form of the blood flow image into orthogonal coordinates from polar coordinates and configured to perform first filter processing for suppressing a noise component included in the electric signal, and the second spatial filter being provided at a post-stage side of the coordinate conversion processing section and configured to perform second filter processing for smoothing an edge of the blood flow image, the filter processing section being configured to change processing contents of at least one of the first filter processing and the second filter processing by linking with switching of the frequency band by the transmission frequency switching section.

7. The ultrasound observation apparatus according to claim 6, wherein the blood flow color creating section changes one of hue and color saturation at a time of visualizing the blood flow image using the one color palette selected by linking with switching of the frequency band by the transmission frequency switching section.

8. The ultrasound observation apparatus according to claim 6, wherein at least one of a filter type, the number of filter taps and a filter coefficient used for filter processing in either the first filter processing or the second filter processing is changed by linking with switching of the frequency band by the transmission frequency switching section.

9. The ultrasound observation apparatus according to claim 6, wherein at least one of a filter type, the number of filter taps and a filter coefficient used for filter processing in both the first filter processing and the second filter processing is changed by linking with switching of the frequency band by the transmission frequency switching section.

* * * * *